(12) United States Patent
Del Castillo

(10) Patent No.: US 6,984,052 B1
(45) Date of Patent: Jan. 10, 2006

(54) DRIP CHAMBER ILLUMINATION DEVICE

(76) Inventor: Gil Del Castillo, 3333 Dominion, #721, Katy, TX (US) 77450

( * ) Notice: Subject to any disclaimer, the term of this patent is extended or adjusted under 35 U.S.C. 154(b) by 261 days.

(21) Appl. No.: 10/268,416

(22) Filed: Oct. 11, 2002

(51) Int. Cl.
*F21K 2/00* (2006.01)

(52) U.S. Cl. ..................... 362/34; 362/101; 362/253; 604/251; 604/255

(58) Field of Classification Search .................. 362/34, 362/84, 101, 253, 154; 604/251, 253, 254, 604/255
See application file for complete search history.

(56) References Cited

U.S. PATENT DOCUMENTS

| | | |
|---|---|---|
| 3,217,709 A | 11/1965 | Schneider et al. |
| 3,563,090 A | 2/1971 | Deltour |
| 4,673,397 A | 6/1987 | Lynn et al. |
| 4,832,214 A | 5/1989 | Schrader et al. |
| 5,321,587 A | 6/1994 | Fujita |
| 5,690,612 A | 11/1997 | Lopez et al. |
| 5,843,045 A | 12/1998 | DuPont |
| 6,050,713 A | 4/2000 | O'Donnell |

FOREIGN PATENT DOCUMENTS

WO   WO01/81823 A2 * 11/2001

* cited by examiner

*Primary Examiner*—Stephen Husar
(74) *Attorney, Agent, or Firm*—Egbert Law Offices

(57) ABSTRACT

A device for illuminating a drip chamber of an IV bag including a collar with an inner diameter suitable for affixing around the drip chamber and a chemiluminescent container affixed to the interior surface of the collar. The chemiluminescent container serves to emit light therefrom and into the drip chamber. A magnifying lens extends upwardly from the collar so as to magnify an interior of the drip chamber.

14 Claims, 2 Drawing Sheets

DRIP CHAMBER ILLUMINATION DEVICE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to devices for illuminating the drip chamber associated with IV bags. For particular, the present invention relates to chemiluminescent techniques for illumination of the interior of such drip chambers. Additionally, the present invention relates to devices for magnifying the interior of the drip chamber.

BACKGROUND OF THE INVENTION

IV fluids are generally supplied to a patient under the force of gravity by positioning a container containing the IV fluid at an elevated position relative to the patient. The rate of flow is set by a manually adjustable clamp positioned in the line between the bag and the patient. The fluid flows from the reservoir to the patient via a drip chamber attached to the lower, or outlet end, of the IV bag. The drip chamber includes a drop former which operates to generate discrete, successive drops which fall from the drop former into a reservoir defined at the lower end of the drip chamber from which fluid flows to the patient via an IV delivery tube. The drip chamber is transparent so that the drips may observed by an anesthesiologist or other medical personnel to insure that drippage is occurring and to further insure that the drippage rate is within appropriate predetermined limits.

It is especially critical that a proper rate be maintained and verified during surgical procedures. However, an increasing number of surgical procedures are being performed in a darkened operating room where the only light is a concentrated, local light at the site of the surgery. Under these conditions, it is virtually impossible to visually determine that drippage is, in fact, occurring and/or is occurring at the predetermined satisfactory rate.

In the past, various patents have issued with respect to devices for illuminating such drip chambers of IV bags. For example, U.S. Pat. No. 3,217,709, issued on Nov. 16, 1965 to Schneider et al., describes a drip meter with a reflector for facilitating the countability of transparent and translucent drops of liquid at low levels of general illumination. The device slips a resilient clip around the drip chamber. The resilient clip has a reflective surface facing the cental axis of the drip former at that stratum where the drips are formed. A small flashlight can be directed to the reflective surface associated with such clip so as to allow the user to determine the drip rate from the IV bag.

U.S. Pat. No. 3,563,090, issued on Feb. 16, 1971, to V. Deltour, describes a drop monitor for monitoring the flow of intravenous feeding. As successive drops fall pass a sensing point, a signal is initiated that it is made to endure for a period longer than the period required for the drop to pass the sensing point. An electro-optical sensing and indicating system causes the presence of a drop at the sensing point to modify a quantity of light reaching a light-sensitive sensor from a source.

U.S. Pat. No. 4,673,397, issued on Jun. 16, 1987 to Lynn et al., describes a medical fluid administration set and drip chamber. A clip is fastened around the exterior drip chamber and light is secured to the clip. The reflection of the drip across the light beam will cause a sensing of the drip rate associated with the drip chamber. The device utilizes a matte finish to alter the surface characteristic between the solution residing in the drip chamber and the drip chamber itself so as to prevent substantially upward splash back or bounce back of liquid drops impacting the surface the fluid in the drip chamber.

U.S. Pat. No. 5,843,045, issued on Dec. 1, 1998 to F. S. DuPont, describes an infusion illuminator in the form of a lamp assembly having a housing, batteries positioned within the housing, a light source positioned in the housing empowered by the battery, a switch controlling the delivery of power from the batteries to the light source, and a clamp for releasably attaching the lamp to the upper end of the drip chamber. A rod extends downwardly from the clamp to position the lamp housing in freestanding relation to the drip chamber with the light source positioned proximate to but spaced from the drip chamber so that the light source is operative to illuminate the drip chamber and to verify the presence of a drippage flow.

U.S. Pat. No. 6,050,713, issued on Apr. 18, 2000 to O'Donnell et al., describes an intravenous drip lighting device for illuminating the drip chamber of intravenous bags during medical precesses that are preformed in a darkened atmosphere. The apparatus utilizes an adjustable pole that supports an intravenous bag support that is capable of holding multiple bags and a plate that supports a fiberoptic light housing which illuminates all drip chambers adequately with equally and differing colored light.

U.S. Pat. No. 5,690,612, issued on Nov. 25, 1997 to Lopez et al., describes a medical connection indicator with a light emitting device that is attached to a medical implement. The light emitting device is connected to the medical implement so as to provide illumination for the connection of other implements thereto. The emission of light in the dark environment of the operating room can facilitate the ability to make the proper connections through the use of the device.

U.S. Pat. No. 4,832,214, issued on May 23, 1989 to Schrader et al., describes a glowing baby bottle nipple collar so as to facilitate the ability of the baby bottles to be retrieved in the dark without the aid of light. The retaining collar of the nipple can absorb and store light from any natural or incandescent light source and emit that light for an extended period of time.

U.S. Pat. No. 5,321,587, issued on Jun. 14, 1994 to M. Fujita, describes a chemiluminescent device having a cylindrical, transparent and flexible container with a hollow and a groove capable of clamping to tubular articles. A ampule is provided in the hollow and contains two liquid substances for chemiluminescent. the liquid substances are capable of performing chemiluminescent when mixed with each other in the container.

It is an object of the present invention to provide a drip chamber illumination device which illuminates the interior of the drip chamber.

It is another object of the present invention to provide a device which provides illumination without the need for electrical connections.

It is another object of the present invention to provide an illumination device which is disposable subsequent to use.

It is another object of the present invention to provide a drip chamber illumination device which magnifies the interior of the drip chamber.

As a further object of the present invention to provide drip chamber illumination device which can be easily fixed and removed from around the exterior of the drip chamber.

These and other objects and advantages of the present invention will become apparent from a reading of the attached specification and appended claims.

BRIEF SUMMARY OF THE INVENTION

The present invention is a device for illuminating a drip chamber comprised of a collar having an interior suitable for affixing around the drip chamber and a chemiluminescent means affixed to the interior surface of the collar. The chemiluminescent means serves to emit light therefrom and into the drip chamber.

The collar has an opening through a wall thereof. The collar is suitably flexible such that the drip chamber can pass through the opening such that the collar will compressively engage the exterior surface of the drip chamber. The collar has a generally omega-shaped cross-section. The collar has flanged surfaces in generally spaced planar alignment and extending outwardly from the opposite sides of this opening.

The chemiluminescent means includes a container, such as an ampule, fixed onto an interior surface of the collar. This container is suitably bendable so that the chemiluminescent components interior thereof can mix so as to create the chemiluminescent light. The container extends around only a portion of the interior surface of the collar.

A magnifying means extends upwardly from the collar. This magnifying means serves to magnify an interior of the drip chamber. The magnifying means is a tubular magnifying lens having a bottom end affixed within the collar. This tubular magnifying lens has longitudinal opening through a wall thereof so as to allow the magnifying lens to be placed around the drip chamber in a position generally over and above the top of the accumulation area of the drip chamber.

DETAILED DESCRIPTION OF THE INVENTION

Figure 1:
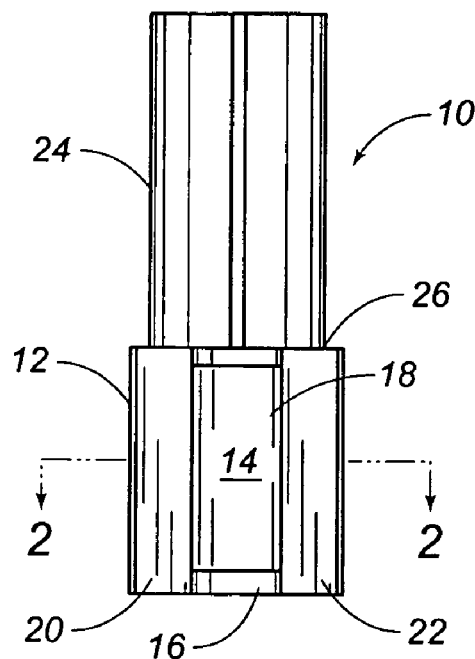
FIG. 1 is a front elevation of the drip chamber illumination device in accordance with the preferred embodiment of the present invention.

Referring to FIG. 1, there is shown the drip chamber illumination device 10 in accordance with the preferred embodiment with the present invention. The device 10 includes a collar 12 having an inner diameter suitable for affixing around the drip chamber and chemiluminescent container 14 affixed to the interior surface 16 of the collar 12. The chemiluminescent container serves to emit light therefrom and into the drip chamber received within the collar 12.

As can be seen in FIG. 1, the collar 12 is formed of polymer-like material and has an opening 18 through one wall thereof. The collar 12 is sufficiently flexible such that the drip chamber can pass through the opening 14 and such that the collar 12 can compressively engage the exterior surface of the drip chamber. The collar 12 has flanged surfaces 20 and 22 in generally planar alignment and extending outwardly on opposite sides of the opening 18.

In FIG. 1, can been seen that a tubular magnifying lens 24 has a bottom end 26 affixed within the collar 12. The magnifying lens 24 extends upwardly from the collar 12 and is configured so as to magnify an interior of the drip chamber. The tubular magnifying lens 24 will have a suitable split through a wall thereof so as to facilitate the ability to place the magnifying lens 24 around the drip chamber.

Figure 2:
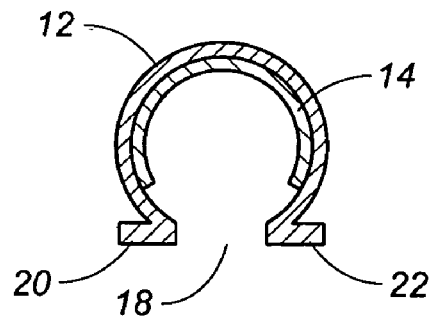
FIG. 2 is a crossed-sectional view taken across lines 2—2 of FIG. 1.

FIG. 2 is a cross-sectional view of the collar 12, the reflective surface 28 formed on the interior surface of the collar 12, and the chemiluminescent container 14. In FIG. 2, can be seen that the collar 12 has a generally omega-shaped cross-section. In particular, flanged surfaces 20 and 22 extend in planar alignment on opposite sides of the opening 18. The collar 12 is configured so as to be sufficiently flexible such that the drip chamber can be pushed through the opening 18 so as to reside within the interior of the collar 12. The flanged surfaces 20 and 22 extend outwardly from opposite sides of the opening 18 so as to further facilitate the application and removal of the collar 12 from the exterior surface of the drip chamber placed therein.

Figure 3:
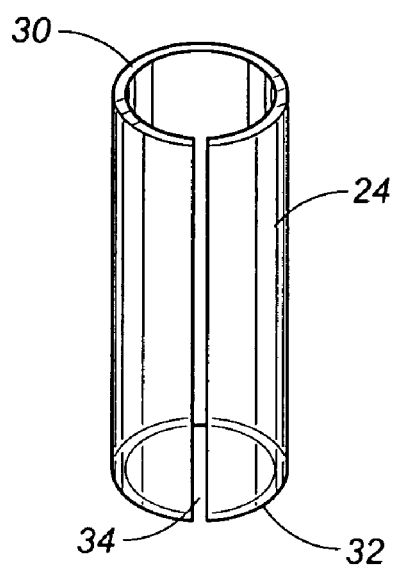
FIG. 3 is an isolated perspective view showing the tubular magnifying lens associated with the drip chamber illumination device of the present invention.

FIG. 3 is and isolated view of the magnifying lens 24. Magnifying lens 24 has an upper end 30 and a lower end 32. The lower end 32 can be received within the interior of the collar 12. A split 34 is formed longitudinally along the tubular magnifying lens 24 so as to facilitate the application and removal of the magnifying lens 24 from the drip chamber. The magnifying lens 24 is suitably configured so as to magnify the image of the drops falling within the drip chamber. The magnifying lens 24 also magnifies the contacting of the particular drops with the meniscus at the top layer of the accumulated liquid. As a result, the contact between the drop and the meniscus particularly visually enhanced. The combination of the light emitted from the chemiluminescent container 14 and the magnifying lens 24 further enhances the imagery associated with the enlargement and illumination of the interior of the drip chamber. Magnifying lens 24 should be sufficiently clear as to enhance visually effects.

Figure 4:
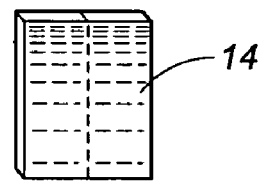
FIG. 4 is an isolated view of the container of chemiluminescent components.

FIG. 4 shows the chemiluminescent container 14. The chemiluminescent container 14 can take on a wide variety of configurations. In FIG. 4, chemiluminescent container 14 has a generally rectangular configuration. However, in alternative embodiments, the chemiluminescent container 14 can be of a disk shape or of other configurations. It is only important that a suitable light-emitting chemiluminescent container of sufficient size be provided which fits within the interior of the collar 12. Chemiluminescent container 14 contains chemiluminescent liquid substances that produce chemiluminescent when mixed. The container 14 contains the chemiluminescence liquid substances such that when container 14 is suitably bent or otherwise manipulated, the substances will mix on the interior of the container. The two chemiluminescent liquid substances are generally a fluorescent liquid and an oxidizing liquid. The fluorescent liquid is composed of dibutylphthalate, a fluorescent substance, and a reaction substance. The oxidizing liquid is composed of dimethylphthalate, hydrogen dioxide, sodium salicylate and the like. Various other chemiluminescent liquid substances could also be used so as to create the illumination effect. The seal between the components can be broken by pushing and pulling on the flanged surfaces 22 and 24 or automatically when the flanged surfaces, associated with opening 18, are separated from each other during the installation of the collar 12 onto the drip chamber. Still further, and alternatively, a direct manipulation of the chemiluminescent container 14 can be made so as to break the seal between the substances prior to installing the chemiluminescent container 14 onto the interior surface of the collar 12. Also and furthermore, the compressive contact between the drip chamber and the surface of the chemiluminescent container can break the seal so as to cause the chemiluminescent effect.

Figure 5:
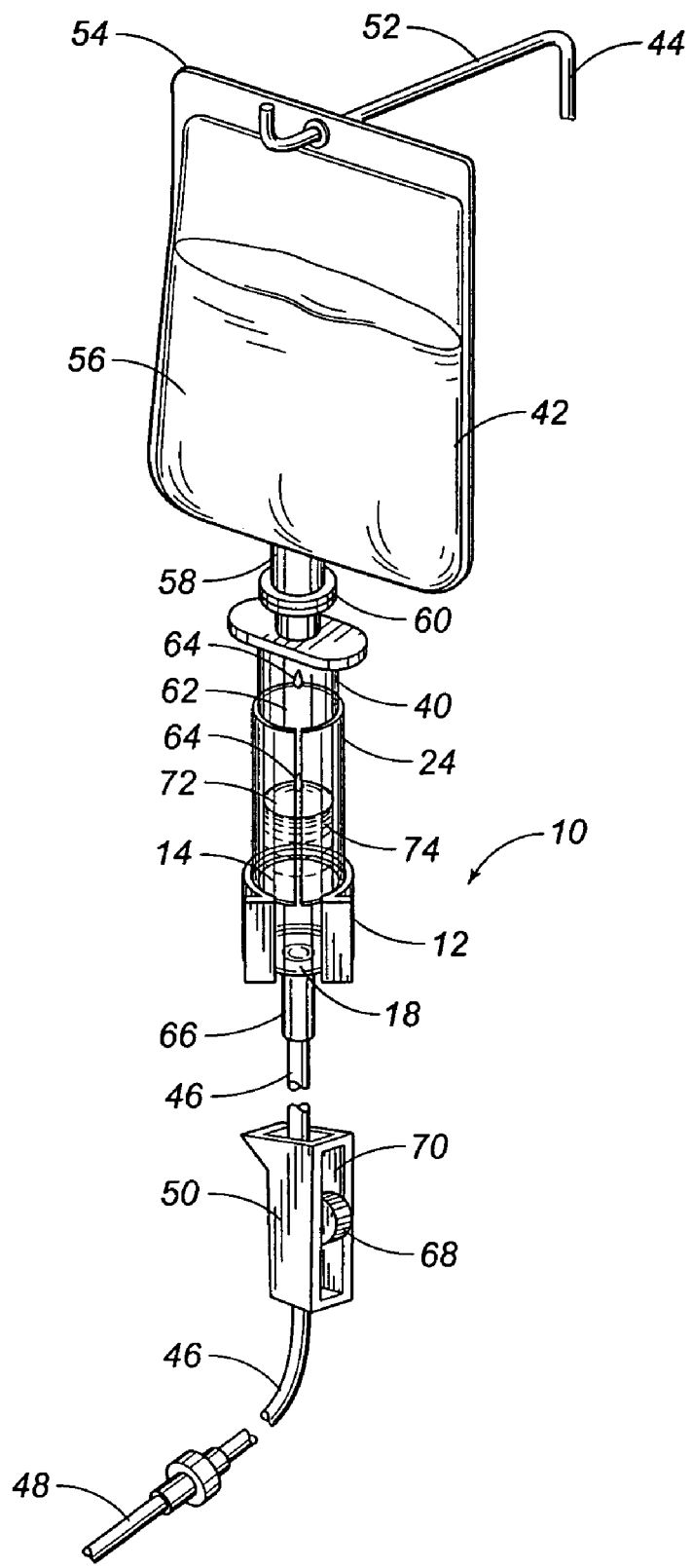
FIG. 5 is a perspective view showing the application of the present invention onto the surface of the drip chamber associated with the IV bag.

FIG. 5 shows the installation of the drip chamber illumination device 10 of the present invention onto a drip chamber 40. In FIG. 5, the IV bag 42 includes a stand 44, the drip chamber 40, the delivery tube 46, a catheter 48 and a flow regulator 50. The stand 44 is of a known form and includes a upper hook structure 52 adapted to hangingly support the bag 42. Bag 42 is formed of a suitable transparent plastic material and is hangingly supported at its upper end 54 by hook 52. The bag 42 will contain a desired intravenous fluid, such as a saline solution 56. Bag 42 includes an outlet 58 of the lower end of the bag 42. Outlet 58 communicates at its upper end with the interior of the bag 42 and terminates in a lower flange 60. The drip chamber 40 is in the form of cylindrical, transparent plastic tube 62 fitted at its upper end over a drop former so as to produce drops 64.

The delivery tube 46 plugs at its upper end to the drip chamber nipple 66 is secured at its lower end to the catheter 48. The catheter 48 is adapted for insertion into a patient body part utilizing a starter needle, in a known manner. The flow regulator 50 is mounted on an intermediate portion of the delivery tube 46 and includes a wheel 68 moving in a slot 70 operative in a known manner to selectively squeeze the delivery tube 46 and thereby control the rate of fluid flow through the delivery tube 46 in response to selective movement of the wheel 68 within the slot 70.

In the present invention, the collar 12 is affixed around the lower portion of the cylindrical transparent plastic tube 62 associated with drip chamber 40. As can be seen, the diameter of the tube 62 is greater than the space between the flanged surfaces 20 and 22 at the opening 18 of the collar 12. As a result, the collar 12 will suitably flex so as to allow the plastic tube 62 to be passed between the flanged surfaces 20 and 22 and into the interior of the collar 12. The magnifying lens 24 extends upwardly from the collar 12 so as to magnify the image of the drops 64 and the meniscus 72 formed at the top of the accumulated liquid 74 within drip chamber 40. The chemiluminescent container 14 is illustrated as positioned on the opposite side of the collar 12 from the opening 18. When the chemiluminescent container 14 is suitably flexed so as to mix the chemiluminescent components therein, light will be emitted so as to illuminate the accumulated liquid 74 within the drip chamber 40 and to provide visual information to the user as to the status of drip flow within the drip chamber 40.

Subsequent to use, the collar 12 can be simply pushed off the drip chamber 40 and disposed of in a conventional manner. Since the chemiluminescent container 14 has only a limited life for the components, it is very difficult to accidentally to re-use the device 10 of the present invention.

The foregoing disclosure and description of the invention is illustrative and explanatory thereof. Various changes in the details of the illustrated apparatus can be made within the scope of the appended claims without departing from the true spirit of the invention. The present invention should only be limited by the following claims and their legal equivalents.

I claim:

1. A device for illuminating a drip chamber comprising:
a collar having an inner diameter suitable for fixing around the drip chamber, said collar having a interior surface; and
a chemiluminescent means affixed to said interior surface of said collar, said chemiluminescent means for emitting light therefrom and into the drip chamber, said collar having an opening through a wall thereof, said collar being flexible such that the drip chamber can pass through said opening and such that said collar can compressively engage an exterior surface of the drip chamber, said collar having an omega-shaped cross section.

2. The device of claim 1, said collar having flanged surfaces in generally planar alignment extending outwardly on opposite sides of said opening.

3. The device of claim 1, said chemiluminescent means comprising;
a container affixed onto an interior surface of said collar, said container being bendable such that chemiluminescent components interior of said container can mix.

4. The device of claim 3, said container extending around only a portion of said interior surface of said collar.

5. A device for illuminating a drip chamber comprising:
a collar having an inner diameter suitable for fixing around the drip chamber, said collar having a interior surface; and
a chemiluminescent means affixed to said interior surface of said collar, said chemiluminescent means for emitting light therefrom and into the drip chamber; and
magnifying means extended upwardly from said collar, said magnifying means for magnifying an interior of the drip chamber.

6. The device of claim 5, said magnifying means comprising:
a tubular magnifying lens having a bottom end affixed within said collar.

7. The device of claim 6, said tubular magnifying lens having a longitudinal split extending through a wall thereof.

8. An apparatus comprising:
an IV bag having a drip chamber at the bottom thereof, said drip chamber having a fluid accumulation area interior thereof;
a collar affixed around said drip chamber adjacent said fluid accumulation area; and
a chemiluminescent means interposed between an exterior surface said drip chamber and an interior surface of said collar, said chemiluminescent means for emitting light therefrom and into said drip chamber.

9. The apparatus of claim 8, further comprising:
a magnifying means extending upwardly from said collar, said magnifying means for magnifying an interior of said drip chamber.

10. The apparatus of claim 9, said magnifying means comprising a tubular magnifying lens having a bottom end affixed within said collar, said tubular magnifying lens extending over a portion of said fluid accumulation area.

11. The apparatus of claim 8, said collar having an opening through one wall thereof, said collar being flexible such that said drip chamber can pass through said opening so that said collar can compressively engage an exterior surface of said drip chamber.

12. The apparatus of claim 11, said collar having an omega-shaped cross section.

13. The apparatus of claim 12, said collar having flanged surfaces in generally spaced planar alignment and extending outwardly from opposite sides of said opening.

14. The apparatus of claim 8, said chemiluminescent means comprising:
   a container affixed onto said interior surface of said collar, said container being bendable such that said chemiluminescent components interior thereof can mix.

* * * * *